United States Patent
Ebata

(10) Patent No.: US 10,758,128 B2
(45) Date of Patent: Sep. 1, 2020

(54) PHOTOACOUSTIC MEASUREMENT APPARATUS AND SYSTEM

(71) Applicant: FUJIFILM Corporation, Tokyo (JP)

(72) Inventor: Tetsurou Ebata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 391 days.

(21) Appl. No.: 15/699,599

(22) Filed: Sep. 8, 2017

(65) Prior Publication Data
US 2017/0367587 A1 Dec. 28, 2017

Related U.S. Application Data

(63) Continuation of application No. PCT/JP2016/001480, filed on Mar. 15, 2016.

(30) Foreign Application Priority Data

Mar. 30, 2015 (JP) ................. 2015-068526

(51) Int. Cl.
 A61B 5/00 (2006.01)
 A61B 8/06 (2006.01)
 A61B 8/00 (2006.01)
 A61B 5/026 (2006.01)
 (Continued)

(52) U.S. Cl.
 CPC .......... *A61B 5/0095* (2013.01); *A61B 5/0261* (2013.01); *A61B 5/742* (2013.01);
 (Continued)

(58) Field of Classification Search
 CPC ... A61B 5/0093; A61B 5/0095; A61B 5/0261; A61B 5/742; A61B 8/06; A61B 8/08;
 (Continued)

(56) References Cited

U.S. PATENT DOCUMENTS

2003/0171668 A1 9/2003 Tsujino et al.
2005/0101846 A1 5/2005 Fine et al.
2012/0014588 A1 1/2012 Chono

FOREIGN PATENT DOCUMENTS

JP 2009-506871 A 2/2009
JP 2012-113191 A 6/2012
(Continued)

OTHER PUBLICATIONS

Extended European Search Report, dated Apr. 20, 2018, for corresponding European Application No. 16771674.5.
(Continued)

*Primary Examiner* — Carolyn A Pehlke
(74) *Attorney, Agent, or Firm* — Birch, Stewart, Kolasch & Birch, LLP

(57) ABSTRACT

A subject is avascularized while changing the avascularization pressure between the avascularized condition and the non-avascularized condition. A receiving circuit receives a detection signal obtained by detecting a photoacoustic wave generated in the subject by emission of measurement light to the subject. Photoacoustic image generating circuitry generates a photoacoustic image based on the detection signal of the photoacoustic wave. The motion of each of a plurality of control points set in each photoacoustic image is detected based on photoacoustic images at a plurality of times. A region of interest is set based on the motion detected at each control point. Blood flow information is generated based on the signal strength of the photoacoustic image in the region of interest.

18 Claims, 12 Drawing Sheets

(51) Int. Cl.
*A61B 8/08* (2006.01)
*G06T 7/00* (2017.01)

(52) U.S. Cl.
CPC ............... *A61B 8/06* (2013.01); *A61B 8/429* (2013.01); *A61B 8/4416* (2013.01); *A61B 8/461* (2013.01); *A61B 8/469* (2013.01); *G06T 7/0012* (2013.01); *A61B 8/08* (2013.01); *A61B 8/4488* (2013.01)

(58) Field of Classification Search
CPC ......... A61B 8/429; A61B 8/441; A61B 8/461; A61B 8/469; A61B 8/4488
See application file for complete search history.

(56) References Cited

FOREIGN PATENT DOCUMENTS

| | | |
|---|---|---|
| JP | 2013-48739 A | 3/2013 |
| JP | 2013-63259 A | 4/2013 |
| JP | 2014-136102 A | 7/2014 |
| JP | 2014-136103 A | 7/2014 |

OTHER PUBLICATIONS

Jaeger et al., "Reduction of Background in Optoacoustic Image Sequences Obtained Under Tissue Deformation," Journal of Biomedical Optics, vol. 14, No. 5, Sep./Oct. 2009 (Jan. 1, 2009), pp. 054011-1 to 054011-10, XP055087210.

Mallidi et al., "Measurement of Blood Perfusion Using Photoacoustic, Ultrasound and Strain Imaging," Proc. of SPIE, vol. 6437, 2007 (Feb. 8, 2007), pp. 643707-1- to 643707-9, XP055056679.

International Search Report (Form PCT/ISA/210) issued in International Application No. PCT/JP2016/001480 dated Jun. 7, 2016, together with an English translation.

Written Opinion of the International Searching Authority (Form PCT/ISA/237) issued in International Application No. PCT/JP2016/001480 dated Jun. 7, 2016, together with an English translation.

PHOTOACOUSTIC MEASUREMENT APPARATUS AND SYSTEM

CROSS-REFERENCE TO RELATED APPLICATIONS

This application is a continuation application of International Application No. PCT/JP2016/001480, filed Mar. 15, 2016, the disclosure of which is incorporated herein by reference in its entirety. Further, this application claims priority from Japanese Patent Application No. 2015-068526, filed Mar. 30, 2015, the disclosure of which is incorporated herein by reference in its entirety.

BACKGROUND OF THE INVENTION

1. Field of the Invention

The present invention relates to a photoacoustic measurement apparatus and system, and more particularly, to a photoacoustic measurement apparatus and system for detecting photoacoustic waves generated in a subject after emitting light to the subject.

2. Description of the Related Art

As a prior art that restricts a blood flow from the outside and releases the restriction to evaluate the perfusion state of the blood flow, a skin perfusion pressure (SPP) measuring apparatus is known (for example, JP2009-506871A). The SPP measuring apparatus emits laser light to a measurement part. The amount and the Doppler shift of reflected light with respect to the emitted laser light change according to a blood flow. The SPP measuring apparatus measures the amount and the Doppler shift of reflected light while changing the cuff pressure from high pressure to low pressure, calculates a cuff pressure at which the blood flow abruptly increases, and displays the cuff pressure as "skin perfusion pressure".

For the observation of the blood flow, JP2012-113191A discloses a method of generating a blood flow image. In JP2012-113191A, a blood flow image is generated by capturing the skin as a motion picture using a reflection type confocal laser microscope, generating a plurality of brightness difference images between frames of the motion picture, and adding the plurality of brightness difference images. JP2012-113191A discloses temporarily stopping (ischemia) the skin blood flow of the forearm (measurement part), which is distal when viewed from the heart, by wrapping a cuff around the subject's upper arm and pressing it and then releasing the pressure to return to the skin blood flow (reperfusion). JP2012-113191A discloses generating a blood flow image before ischemia, during ischemia, and immediately after reperfusion.

SUMMARY OF THE INVENTION

In JP2009-506871A, since the blood flow is measured at one measurement point, it is not possible to evaluate the spatial distribution of perfusion. In particular, it is not possible to perform evaluation in a depth direction. In JP2012-113191A, it is possible to evaluate the spatial distribution of perfusion with a blood flow image. In JP2012-113191A, however, since observation is performed using a reflection type confocal laser microscope, only the vicinity of the skin surface can be mainly observed.

Here, as a kind of image examination method capable of examining the state of the inside of a living body from the skin surface to a deeper place in a non-invasive manner, photoacoustic imaging for imaging the inside of the living body by using the photoacoustic effect is known. In general, in photoacoustic imaging, pulsed laser light is emitted into the living body. In the living body, a living tissue absorbs the energy of the pulsed laser light, and ultrasound waves (photoacoustic waves) are generated due to adiabatic expansion due to the energy. By detecting the photoacoustic waves using an ultrasound probe or the like and generating a photoacoustic image based on the detection signal, it is possible to visualize the inside of the living body based on the photoacoustic waves.

It is an object of the present invention to provide a photoacoustic measurement apparatus and system capable of setting a region of interest, which is useful for the evaluation of blood flow, using the above-described photoacoustic image.

In order to achieve the aforementioned object, the present invention provides a photoacoustic measurement apparatus comprising: a receiving circuit that receives a detection signal obtained by detecting a photoacoustic wave generated in a subject by emission of measurement light to the subject; photoacoustic image generation means for generating a photoacoustic image based on the detection signal of the photoacoustic wave; motion detection means for detecting motion of each of a plurality of control points set in a plurality of the photoacoustic images, which are generated by emitting the measurement light to the subject at a plurality of times between an avascularized condition and a non-avascularized condition, using the plurality of photoacoustic images; region of interest setting means for setting a region of interest based on motion detected at each control point included in a position range including the plurality of control points; and blood flow information generation means for generating blood flow information based on a signal strength of the photoacoustic image in the region of interest.

In addition, the present invention provides a photoacoustic measurement apparatus comprising: a receiving circuit that receives a detection signal of a photoacoustic wave generated in a subject by emission of measurement light to the subject and a detection signal of a reflected acoustic wave of an acoustic wave transmitted to the subject; photoacoustic image generation means for generating a photoacoustic image based on the detection signal of the photoacoustic wave; reflected acoustic wave image generation means for generating a reflected acoustic wave image based on the detection signal of the reflected acoustic wave; motion detection means for detecting motion of each of a plurality of the reflected acoustic wave images, which are generated by transmitting the acoustic wave to the subject at a plurality of times between an avascularized condition and a non-avascularized condition, at a plurality of positions corresponding to a plurality of control points set in the photoacoustic image using the plurality of reflected acoustic wave images and detecting the detected motion at each position as motion of each control point set in the photoacoustic image; region of interest setting means for setting a region of interest based on motion detected at a control point included in a position range including a plurality of the control points; and blood flow information generation means for generating blood flow information based on a signal strength of the photoacoustic image in the region of interest.

In the photoacoustic measurement apparatus of the present invention, a plurality of region of interest candidates may be set in a lattice form in the photoacoustic image, and each region of interest candidate may include the plurality of control points. The region of interest setting means may determine a region, which is to be set as the region of interest, among the plurality of region of interest candidates.

The region of interest setting means may set the region of interest by determining a region of interest candidate to be excluded from the region of interest and setting remaining regions of interest candidates as regions of interest.

Based on motion detected at each control point included in each region of interest candidate, the region of interest setting means may determine whether or not to exclude the region of interest candidate from the region of interest.

The region of interest setting means may determine whether or not the motion detected at each of the plurality of control points included in the position range satisfies predetermined conditions and determine the region of interest candidate to be excluded based on the determination result.

In the above, in a case where the motion detected at each of the plurality of control points included in the position range including the plurality of control points satisfies the predetermined conditions, the region of interest setting means may determine whether or not motion detected at each of a plurality of control points including control points adjacent to the position range satisfies the predetermined conditions and enlarge the position range until the conditions are not satisfied.

The region of interest setting means may determine whether or not the motion detected at each of the plurality of control points included in the position range including the plurality of control points satisfies the predetermined conditions in a predetermined time range and determine the region of interest candidate to be excluded based on the determination result.

In the above, in a case where the motion detected at each of the plurality of control points included in the position range satisfies the predetermined conditions in the predetermined time range, the region of interest setting means may determine whether or not motion detected at each of a plurality of control points including a time before and after the time range satisfies the predetermined conditions and enlarge the time range until the conditions are not satisfied.

The region of interest setting means may determine a region of interest candidate, which includes a position range where the motion detected at each of the plurality of control points satisfies the predetermined conditions, as the region of interest candidate to be excluded.

The conditions may include at least one of conditions in which an amount of motion detected at each of the plurality of control points is equal to or greater than a threshold value and each of a difference in a direction of the motion detected at each of the plurality of control points and a difference in the amount of motion detected at each of the plurality of control points is within a threshold value, conditions in which the amount of motion detected at each of the plurality of control points is equal to or less than a threshold value, or conditions in which at least one of a degree indicating a variation in the direction of the motion detected at each of the plurality of control points or a degree indicating a variation in the amount of motion detected at each of the plurality of control points is equal to or greater than a threshold value.

Contrary to the above, the region of interest setting means may determine whether or not the motion detected at each of the plurality of control points included in the position range including the plurality of control points satisfies predetermined conditions and set a region of interest candidate, which includes a position range where the motion detected at each of the plurality of control points satisfies the predetermined conditions, as the region of interest.

The blood flow information generation means may generate, as blood flow information, a total value or an average value of the signal strength in the region of interest.

The blood flow information generation means may further generate a graph showing a relationship between the blood flow information and time.

The photoacoustic measurement apparatus of the present invention may further comprise pressure measurement means for measuring an avascularization pressure of the subject. The blood flow information generation means may further generate a graph showing a relationship between the blood flow information and the avascularization pressure.

The blood flow information generation means may further generate a blood flow information image based on the blood flow information.

The present invention provides a photoacoustic measurement system comprising: a light source that emits measurement light; avascularization means for avascularizing a subject while changing avascularization pressure between an avascularized condition and a non-avascularized condition; acoustic wave detection means for detecting a photoacoustic wave generated in the subject by emission of the measurement light to the avascularized subject; photoacoustic image generation means for generating a photoacoustic image based on a detection signal of the photoacoustic wave detected by the acoustic wave detection means; motion detection means for detecting motion of each of a plurality of control points set in a plurality of the photoacoustic images, which are generated by emitting the measurement light to the subject at a plurality of times between the avascularized condition and the non-avascularized condition, using the plurality of photoacoustic images; region of interest setting means for setting a region of interest based on motion detected at each control point included in a position range including the plurality of control points; and blood flow information generation means for generating blood flow information based on a signal strength of the photoacoustic image in the region of interest.

The present invention provides a photoacoustic measurement system comprising: a light source that emits measurement light; avascularization means for avascularizing a subject while changing avascularization pressure between an avascularized condition and a non-avascularized condition; acoustic wave detection means for detecting a photoacoustic wave generated in the subject by emission of the measurement light to the avascularized subject and a reflected acoustic wave of an acoustic wave transmitted to the subject; photoacoustic image generation means for generating a photoacoustic image based on a detection signal of the photoacoustic wave detected by the acoustic wave detection means; reflected acoustic wave image generation means for generating a reflected acoustic wave image based on a detection signal of the reflected acoustic wave detected by the acoustic wave detection means; motion detection means for detecting motion of each of a plurality of the reflected acoustic wave images, which are generated by transmitting the acoustic wave to the subject at a plurality of times between the avascularized condition and the non-avascularized condition, at a plurality of positions corresponding to a plurality of control points set in the photoacoustic image using the plurality of reflected acoustic wave images and detecting the detected motion at each position as motion of each control point set in the photoacoustic image; region of interest setting means for setting a region of interest based on motion detected at each control point included in a position range including the plurality of control points; and blood flow information generation means for generating blood flow information based on a signal strength of the photoacoustic image in the region of interest.

The photoacoustic measurement apparatus and system of the present invention can set a region of interest useful for the evaluation of blood flow.

DESCRIPTION OF THE PREFERRED EMBODIMENTS

The inventors have considered evaluating the perfusion of blood using the photoacoustic image described above. By using short pulsed laser light having a wavelength at which absorption in blood is stronger than that in surrounding tissues, such as muscle or fat, as measurement light, it is possible to detect and image the signal of blood (hemoglobin) by detecting photoacoustic waves generated by absorption using a probe. By using a photoacoustic image, it is possible to draw fine blood vessels that are difficult to draw particularly in ultrasound Doppler. It is thought that the present invention can be applied to the diagnosis of symptoms starting from fine blood vessel lesions, such as stage diagnosis of diabetes or diabetic microvascular complications, by avascularizing the subject while changing the avascularization pressure between the avascularized condition and the non-avascularized condition, emitting measurement light to the subject, detecting a photoacoustic wave generated in the subject by the emission of measurement light, generating a photoacoustic image based on the detection signal of the photoacoustic wave, and observing a time-series change in the signal strength in a certain region of interest in the photoacoustic image.

In the above work, it is considered to divide the entire image of the photoacoustic image in a lattice form at predetermined intervals and set each divided region as a region of interest. In this case, as the number of divisions of the image increases, a large number of regions of interest are set. In a case where a large number of regions of interest are set, if the time-series change in the signal strength in all the regions of interest is displayed as a graph, the amount of information becomes too large. This may make the evaluation difficult. Setting a region of interest to be analyzed manually may be considered. In this case, however, since the photoacoustic image has little structure information of the subject and few features as markers, it is also difficult to determine where the region of interest should be set. Therefore, a photoacoustic measurement apparatus and system for setting a region of interest useful for the evaluation of blood flow is required.

Figure 1:
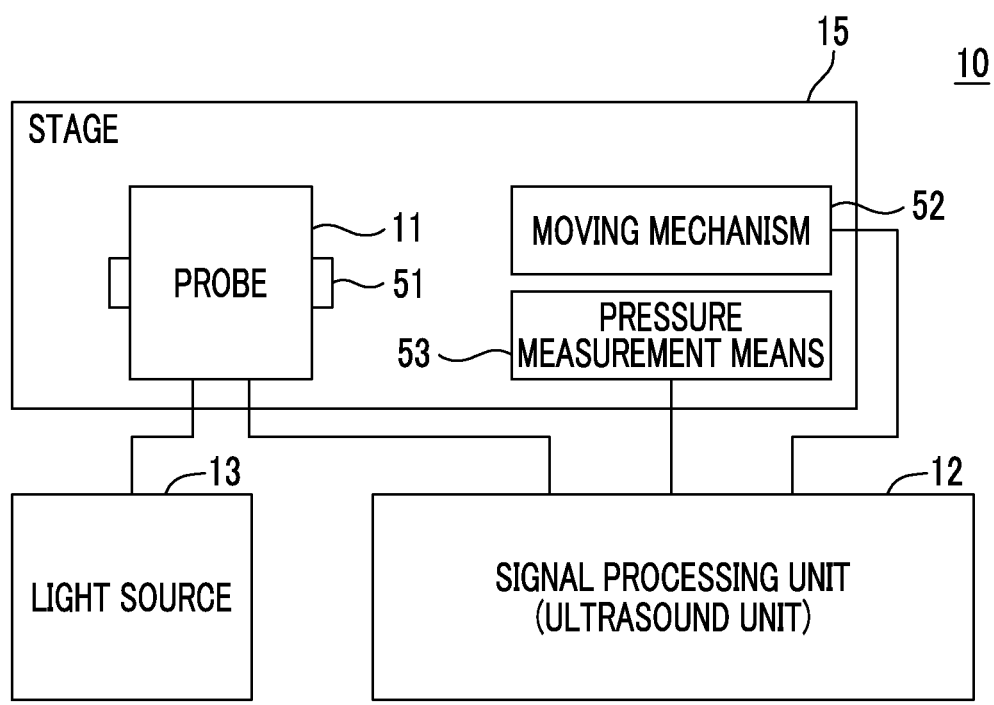
FIG. 1 is a block diagram showing the schematic configuration of a photoacoustic measurement system including a photoacoustic measurement apparatus according to a first embodiment of the present invention.

Hereinafter, an embodiment of the present invention will be described in detail with reference to the diagrams. FIG. 1 shows the schematic configuration of a photoacoustic measurement system including a photoacoustic measurement apparatus according to a first embodiment of the present invention. A photoacoustic measurement system 10 has a probe (ultrasound probe) 11, an ultrasound unit (signal processing unit) 12, a light source 13, and a stage 15.

The light source 13 emits measurement light. The measurement light emitted from the light source 13 is guided to the probe 11 using, for example, light guide means, such as an optical fiber, and is emitted from the probe 11 toward a subject. The light source 13 is, for example, a solid state laser light source using an yttrium aluminum garnet (YAG), alexandrite, or the like. The wavelength of measurement light is preferably a wavelength at which absorption in blood is stronger than that in the surrounding tissue, such as muscle or fat. Hereinafter, an example in which light having a wavelength of 755 nm is mainly used will be described. The type of the light source is not particularly limited, and the light source 13 may be a laser diode light source (semiconductor laser light source), or may be a light amplification type laser light source using a laser diode light source as a seed light source. Light sources other than the laser light source may be used.

The probe 11 is acoustic wave detection means, and has a plurality of detector elements (ultrasound transducers) arranged in a one-dimensional manner, for example. As each detector element, for example, piezoelectric ceramics are used. A piezoelectric element formed of a polymer film, such as polyvinylidene fluoride (PVDF), may be used as each detector element. The probe 11 is not limited to the linear probe, but may be a convex probe or a sector probe. The probe 11 is disposed in a part (measurement part) for measuring the blood perfusion of the subject with echogel, water, or the like interposed therebetween. It is preferable that the probe 11 is disposed on the palm side where the amount of body hair or skin melanin is small.

The probe 11 detects photoacoustic waves generated in the subject by emitting measurement light to the avascularized subject while changing the avascularization pressure between the avascularized condition and the non-avascularized condition. Here, the avascularized condition refers to a state in which the blood flow in the measurement part of the subject is at least partially stopped. Preferably, the avascularized condition refers to a state in which the subject is pressed with a pressure equal to or higher than the systolic blood pressure. The non-avascularized condition refers to a state in which the blood flow in the measurement part of the subject is not disturbed. Preferably, the non-avascularized condition refers to a state in which the subject is not pressed or the subject is pressed with a pressure equal to or lower than the diastolic blood pressure.

The stage 15 is a stage on which the subject is placed. The stage 15 includes a grip portion 51 for gripping the probe 11, a moving mechanism 52 for moving the probe 11 in a direction in which the probe 11 is pressed against the subject and a direction in which the probe 11 is away from the subject through the grip portion 51, pressure measurement means 53 for measuring (detecting) the contact pressure of the probe 11 with respect to the subject. In the present embodiment, the contact pressure (avascularization pressure) of the probe 11 with respect to the subject is changed by moving the probe 11 using the moving mechanism 52.

The ultrasound unit 12 processes the detection signal of photoacoustic waves detected by the probe. The ultrasound unit 12 forms a photoacoustic measurement apparatus. The ultrasound unit 12 typically has a processor, a memory, a bus, and the like.

Figure 2:
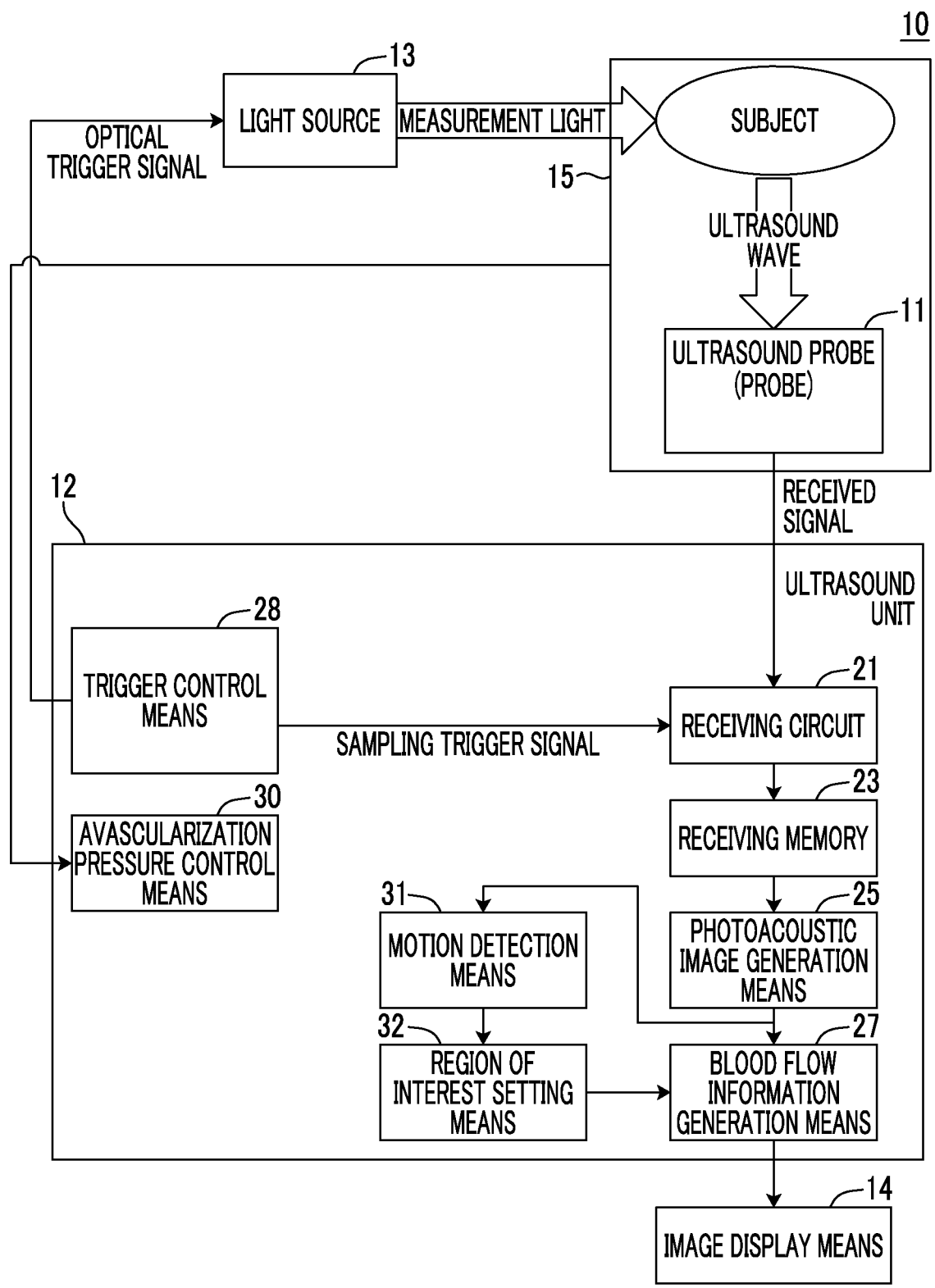
FIG. 2 is a block diagram showing the detailed configuration of the photoacoustic measurement system.

FIG. 2 shows the detailed configuration of a photoacoustic measurement system. In FIG. 2, the grip portion 51, the moving mechanism 52, and the pressure measurement means 53 of the stage 15 are not shown. The ultrasound unit 12 has a receiving circuit 21, a receiving memory 23, photoacoustic image generation means 25, blood flow information generation means 27, trigger control means 28, avascularization pressure control means 30, motion detection means 31, and region of interest setting means 32.

The receiving circuit 21 receives a detection signal output from the probe 11, and stores the received detection signal in the receiving memory 23. Typically, the receiving circuit 21 includes a low noise amplifier, a variable gain amplifier, a low pass filter, and an analog to digital converter (AD converter). The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 23. The receiving circuit 21 is formed by one integrated circuit (IC), for example. As the receiving memory 23, for example, a semiconductor memory is used.

The probe 11 outputs a detection signal of photoacoustic waves, and a detection signal (sampling data) of photoacoustic waves after AD conversion is stored in the receiving memory 23. The photoacoustic image generation means 25 reads the detection signal of photoacoustic waves from the receiving memory 23, and generates a photoacoustic image based on the read detection signal of photoacoustic waves. The generation of a photoacoustic image includes, for example, image reconstruction such as phase matching addition, detection, and logarithmic conversion. For example, the photoacoustic image generation means 25 is formed by large scale integration (LSI), such as a digital signal processor (DSP). The function of the photoacoustic image generation means 25 may be realized by software processing using a processor included in the ultrasound unit 12.

The motion detection means 31 detects the motion of a photoacoustic image based on photoacoustic images at a plurality of times between the avascularized condition and the non-avascularized condition. In the present embodiment, "between the avascularized condition and the non-avascularized condition" includes at least one of end portions of such a range, that is, an avascularized condition or a non-avascularized condition. In other words, in the present embodiment, "a plurality of times between the avascularized condition and the non-avascularized condition" includes a time in a case where the subject is in the avascularized condition or a time in a case where the subject is in the non-avascularized condition. A plurality of control points are set in advance in the photoacoustic image, and the motion detection means 31 detects motion at the plurality of control points. The detected motion includes the direction of motion and the amount of motion. The motion detection means 31 calculates a motion vector between times (frames) before and after avascularization pressure change for each control point, for example. A general optical flow calculation method, such as block matching, can be used to calculate the motion vector of each control point. The motion detection means 31 is, for example, a DSP. The function of the motion detection means 31 may be realized by software processing using a processor included in the ultrasound unit 12.

The region of interest setting means 32 sets a region of interest (ROI) based on the motion of the control point detected by the motion detection means 31. The region of interest setting means 32 determines a region to be set as a region of interest among a plurality of region of interest candidates set in the photoacoustic image, for example. Each region of interest candidate is set in a lattice form in the photoacoustic image. In addition, each region of interest includes a plurality of control points. The region of interest setting means 32 sets regions of interest, for example, by determining region of interest candidates to be excluded from the regions of interest, among a plurality of region of interest candidates, and determining the remaining region of interest candidates as regions of interest. In the setting of a region of interest, based on the motion detected at the control point included in each region of interest candidate, the region of interest setting means 32 determines whether or not to exclude the region of interest candidate from the region of interest. The region of interest setting means 32 is, for example, a DSP. The function of the region of interest setting means 32 may be realized by software processing using a processor included in the ultrasound unit 12.

The blood flow information generation means 27 generates blood flow information based on the signal strength of a photoacoustic image in the region of interest set by the region of interest setting means 32. The blood flow information generation means 27 generates blood flow information by scoring the signal strength of the photoacoustic image in the region of interest, for example. Specifically, a total value or an average value of the signal strength of the photoacoustic image in the region of interest is calculated, and a score value based on the value is generated as blood flow information. The blood flow information generation means 27 may further generate a graph showing the relationship between blood flow information and time. The blood flow information generation means 27 is, for example, a DSP. The function of the blood flow information generation means 27 may be realized by software processing using a processor included in the ultrasound unit 12.

Here, the signal strength of the photoacoustic image is a value corresponding to the magnitude of the detection signal of the detected photoacoustic wave, and does not necessarily need to be the same as the pixel value of the photoacoustic image for display. Any signal in the photoacoustic image generation step can be used as the signal strength of the photoacoustic image. Specifically, a detection signal of photoacoustic waves after reconstruction, a detection signal of photoacoustic waves after detection, and a detection signal of photoacoustic waves after logarithmic conversion may be used as the signal strength of the photoacoustic image.

The blood flow information generation means 27 outputs the generated blood flow information to image display means 14, such as a display device. The blood flow information generation means 27 may output a graph showing the relationship between blood flow information and time to the image display means 14. The blood flow information generation means 27 may display a photoacoustic image and a region of interest on the image display means 14.

The trigger control means 28 controls each unit in the ultrasound unit 12. For example, in the case of acquiring a photoacoustic image, the trigger control means 28 transmits an optical trigger signal to the light source 13 so that measurement light is emitted from the light source 13. In addition, the trigger control means 28 controls the sampling start timing of photoacoustic waves or the like by transmitting a sampling trigger signal to the receiving circuit 21 in response to the emission of the measurement light. The area where photoacoustic waves are to be detected may be divided into a plurality of areas. In this case, emission of light to the subject and detection of photoacoustic waves are performed for each area. For example, the trigger control means 28 is formed by a programmable logic device (PLD), such as a field-programmable gate array (FPGA).

The avascularization pressure control means 30 drives the moving mechanism 52 based on the contact pressure detected by the pressure measurement means 53 (refer to FIG. 1). The avascularization pressure control means 30 changes the contact pressure of the probe 11 by driving the moving mechanism 52. In addition, the contact pressure of the probe 11 is maintained at a certain pressure by driving the moving mechanism 52. As the avascularization pressure control means 30, for example, an FPGA is used.

Measurement is performed in the following procedure. After the subject is placed on the stage 15, the avascularization pressure control means 30 drives the moving mechanism 52 to press the probe 11 against the subject. The avascularization pressure control means 30 moves the probe 11 in a direction in which the probe 11 is pressed against the subject, for example, until the contact pressure detected by the pressure measurement means 53 reaches a pressure equal to or greater than the systolic blood pressure, for example, 200 mmHg. After avascularization of a part to be examined, the trigger control means 28 starts emission of measurement light and detection of photoacoustic waves. The emission of measurement light and the detection of photoacoustic waves are continued while maintaining the avascularized condition. After continuing the avascularized condition for a certain period of time, the avascularization pressure control means 30 drives the moving mechanism 52 to move the probe 11 stepwise in a direction away from the subject. The emission of measurement light and the detection of photoacoustic waves are continued before and after the change in contact pressure. By generating a photoacoustic image based on the detection signal of photoacoustic waves detected at each time, blood flow information is generated. For example, an average value of the signal strength of the photoacoustic image in the region of interest is generated as blood flow information. In the present embodiment, since the probe 11 (an example of avascularization means) performs avascularization of the subject, it is possible to evaluate the perfusion state without using a tourniquet (another examples of avascularization means) separately.

In the avascularized condition, a blood flow in the capillary or the like is stopped. As a result, blood that is a light absorber is no longer present in the region of interest. Since the number of light absorbers present in the region of interest is small, the signal strength of the photoacoustic image of the region of interest is low. In a case where the contact pressure of the probe 11 is reduced stepwise to cause a stepwise change from the avascularized condition to the non-avascularized condition, perfusion of blood to the capillary gradually occurs. Accordingly, the amount of blood present in the region of interest increases gradually. As a result, the signal strength in the region of interest increases compared with that at the time of avascularization. In the non-avascularized condition, perfusion of blood to the capillary occurs, and the amount of blood present in the region of interest is at the same level as before the avascularization. The signal strength in the region of interest further increases to reach a certain level.

Here, the strength of a photoacoustic wave generated in the subject changes depending on the hemoglobin concentration and the oxygen saturation. In a case where light having a wavelength of 755 nm is used as the measurement light, the photoacoustic wave becomes weak as the blood volume decreases, and the photoacoustic wave becomes strong as the blood volume increases. In addition, the photoacoustic wave becomes strong as the oxygen saturation decreases, and the photoacoustic wave becomes weak as the oxygen saturation increases. In a case where the non-avascularized condition is changed to the avascularized condition, the blood volume and the oxygen saturation are reduced. On the other hand, in a case where the avascularized condition is changed to the non-avascularized condition, the blood volume and the oxygen saturation are increased. It is thought that the reason why the signal strength of the photoacoustic image in the region of interest is reduced in the avascularized condition is that a reduction in the detection signal of the photoacoustic wave due to a reduction in blood volume is larger than an increase in the detection signal of the photoacoustic wave due to a reduction in oxygen saturation. In addition, it is thought that the reason why the signal strength of the photoacoustic image in the region of interest increases in the non-avascularized condition is that an increase in the detection signal of the photoacoustic wave due to an increase in blood volume is larger than a reduction in the detection signal of the photoacoustic wave due to an increase in oxygen saturation.

Figure 3:
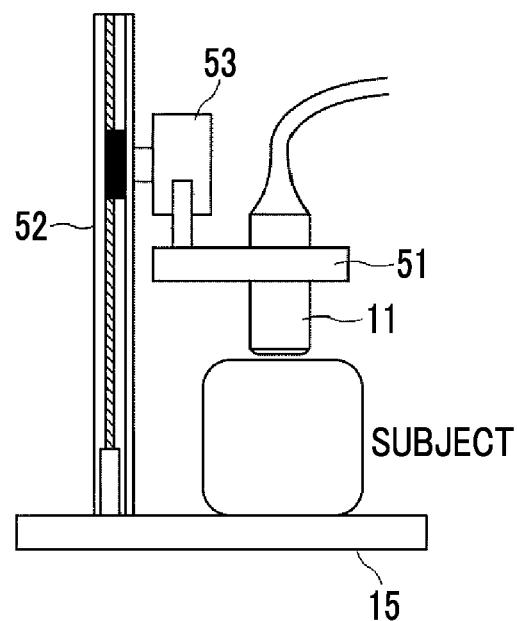
FIG. 3 is a diagram showing an example of detecting a photoacoustic wave by pressing a subject with a probe.

FIG. 3 shows an example of detecting a photoacoustic wave by presses a subject with a probe. The grip portion 51 is, for example, an arm, and grips the probe 11. The moving mechanism 52 includes, for example, a ball screw and a motor for rotating the ball screw. The pressure measurement means 53 is, for example, a pressure sensor, and is provided between a moving portion moved by the ball screw and the grip portion 51. As the pressure sensor, for example, various known ones such as a strain gauge, a load cell, and a piezoelectric film can be used. The pressure measurement means 53 detects the contact pressure of the probe 11 with respect to the subject in the grip portion 51. More specifically, in a connection portion between the grip portion 51 and the moving mechanism 52, the contact pressure of the probe 11 with respect to the subject is detected. The detection signal of the pressure measurement means 53 is transmitted to the ultrasound unit 12.

Figure 4:
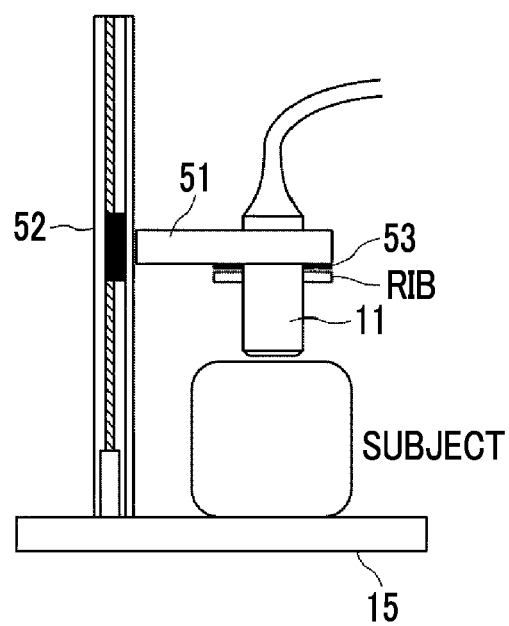
FIG. 4 is a diagram showing another example of detecting a photoacoustic wave by pressing a subject with a probe.

FIG. 4 shows another example of detecting a photoacoustic wave by pressing a subject with a probe. In this example, the pressure measurement means 53 is provided between the rib of the grip portion 51 and the arm. In a case where the probe 11 is moved in the subject direction by the moving mechanism 52, the detection signal of the pressure measurement means 53 is changed by the rib pressing the arm. The position of the pressure measurement means 53 is not particularly limited, and any position is acceptable as long as the contact pressure of the probe 11 with respect to the subject can be detected. It is also possible to adopt a configuration in which the pressure measurement means 53 is provided in the probe 11.

Figure 5:
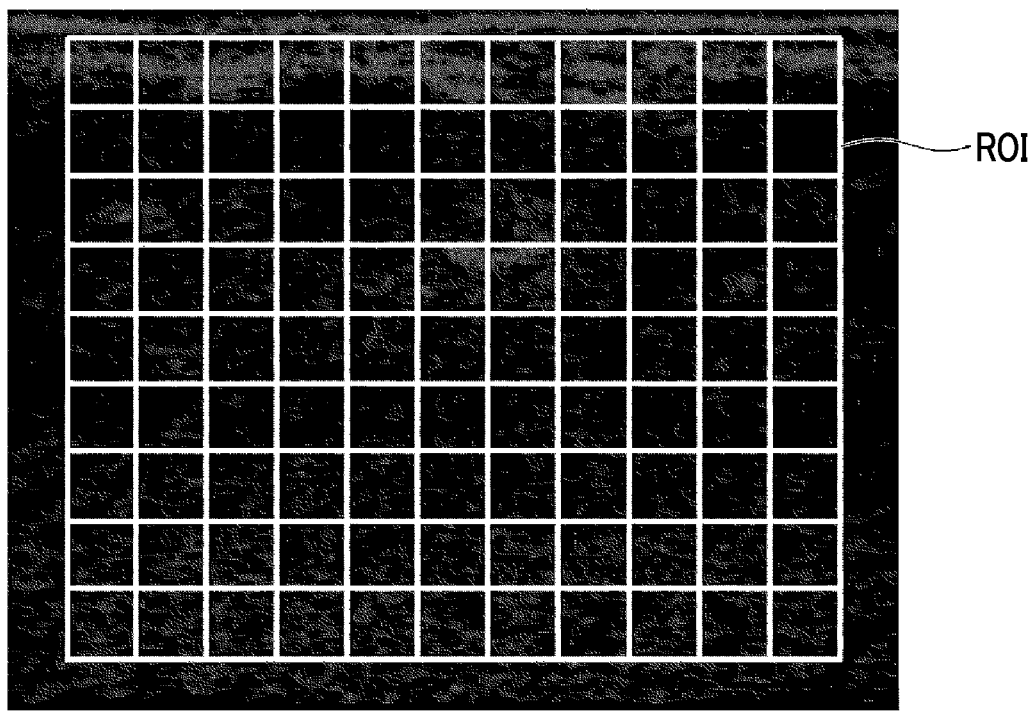
FIG. 5 is a diagram showing region of interest candidates set in a photoacoustic image.

Hereinafter, the motion detection and setting of a region of interest will be described in detail. FIG. 5 shows region of interest candidates set in a photoacoustic image. Each region of interest candidate (ROI candidate) is, for example, a region obtained by dividing a certain region in a photoacoustic image at predetermined intervals. Each region of interest candidate may be a region obtained by dividing the entire photoacoustic image at predetermined intervals. In the example shown in FIG. 5, 11 (horizontal)×9 (vertical) region of interest candidates are set in the photoacoustic image. Regions of interest are set among the region of interest candidates. The aspect ratio of the region of interest candidate does not need to be 1:1, and the region of interest candidate may be a rectangular region. In addition, the region of interest candidate does not need to be a rectangular shape, and the shape is arbitrary.

Figure 6:
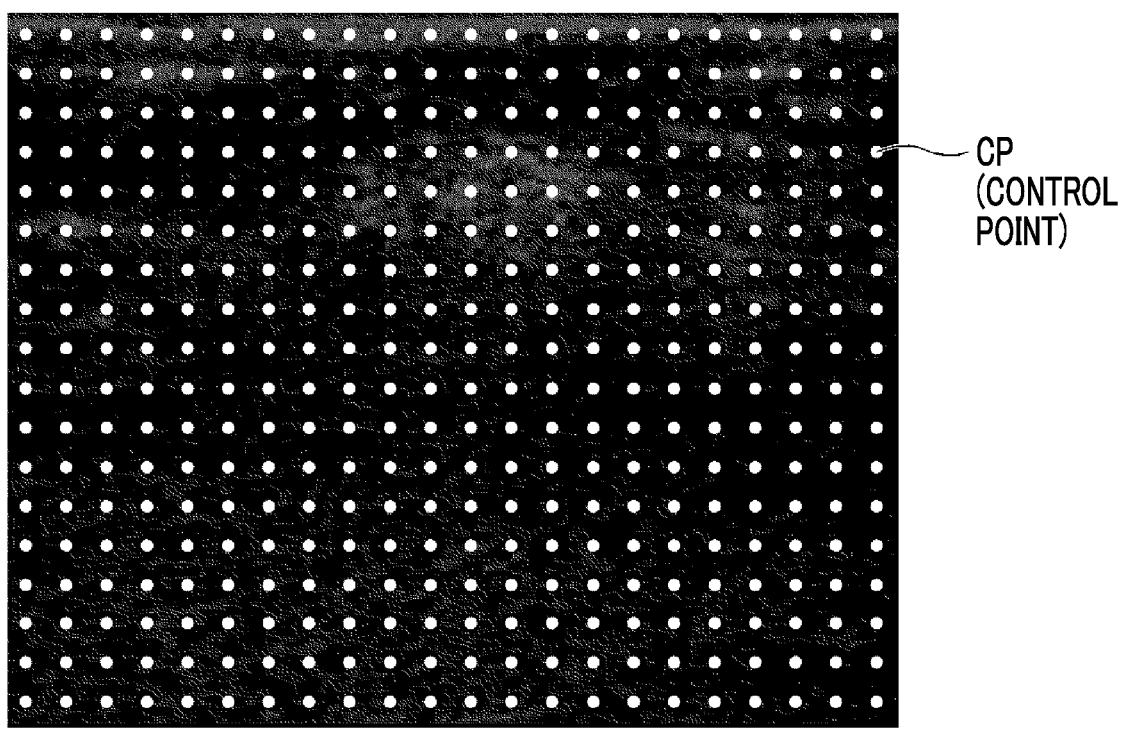
FIG. 6 is a diagram showing control points set in the photoacoustic image.

FIG. 6 shows control points set in a photoacoustic image. Control points CP are set at predetermined intervals in the vertical and horizontal directions in a photoacoustic image, for example. The interval between the control points CP may be different in the vertical and horizontal directions of the image. The interval between the control points CP does not need to be uniform within the image. Each region of interest candidate includes a plurality of control point CP in the region. The motion detection means 31 calculates a motion vector between photoacoustic images, which are consecutively acquired, for each control point CP. The size of each control point CP is not limited to the size shown in FIG. 6, and may be one pixel or several pixels. The correspondence relationship between the control point CP and the size and position of the region of interest candidate is not limited to the correspondence relationship between FIGS. 5 and 6, and it is preferable that each region of interest candidate includes at least one control point.

The region of interest setting means 32 may determine whether or not the motion detected at each of a plurality of control points, which are included in a position range including a plurality of control points, satisfies predetermined conditions and determine region of interest candidates to be excluded from the regions of interest based on the determination result. It is preferable that the size of the position range is smaller than the size of the region of interest candidate. Alternatively, the size of the position range may be the same as the size of the region of interest candidate, or may be larger than the size of the region of interest candidate. The region of interest setting means 32 may determine whether or not the motion detected at each of a plurality of control points included in the position range satisfies predetermined conditions in a predetermined time range and determine region of interest candidates to be excluded from the regions of interest based on the determination result.

Figure 7:
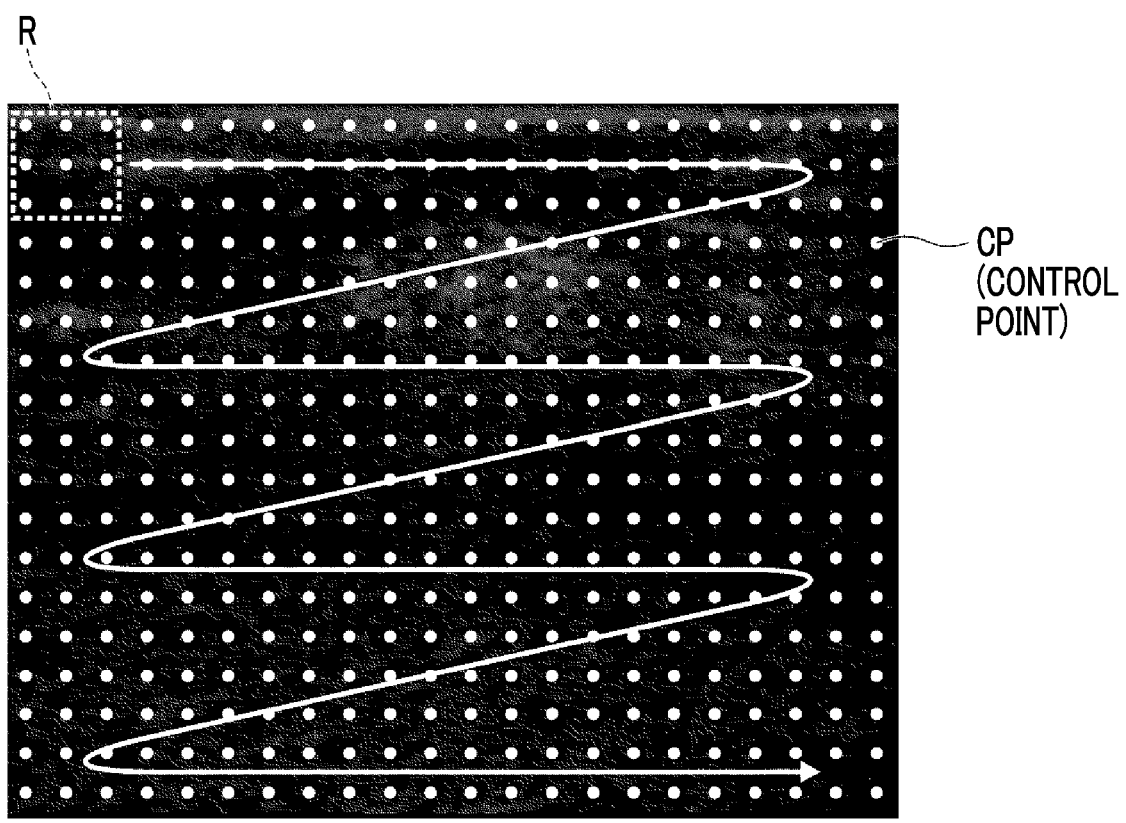
FIG. 7 is a diagram showing control points and a position range including a plurality of control points.

FIG. 7 shows control points and the above-described position range. The size of the position range R, that is, the number of control points included in the position range R, is set in advance. In the example shown in FIG. 7, the position range R includes three control points in each of the horizontal direction and the vertical direction of the image. While scanning the position range R including the 3×3 control points over the image, the region of interest setting means 32 determines whether or not the motion detected at each of a plurality of control points included in the position range R satisfies predetermined conditions at each scan position. For example, the region of interest setting means 32 scans the position range R over the entire image by raster-scanning the position range R including 3×3 control points while shifting the position of the control point at the center of the position range R one by one from the upper left to the lower right of the image in the diagram.

The region of interest setting means 32 determines, for example, a region of interest candidate including a position range, in which the motion detected at each of a plurality of control points satisfies predetermined conditions, as a region of interest candidate to be excluded from the regions of interest. On the contrary, a region of interest candidate including a position range, in which the motion detected at each of a plurality of control points included in the position range satisfies predetermined conditions, may be set as a region of interest.

The predetermined conditions include, for example, at least one of conditions in which the amount of motion detected at each of a plurality of control points included in the position range is equal to or greater than a threshold value and each of a difference in the direction of the motion detected at each of a plurality of control points and a difference in the amount of motion detected at each of a plurality of control points is within a threshold value (conditions A), conditions in which the amount of motion detected at each of a plurality of control points is equal to or less than a threshold value (conditions B), or conditions in which at least one of a degree indicating a variation in the direction of the motion detected at each of a plurality of control points or a degree indicating a variation in the amount of motion detected at each of a plurality of control points is equal to or greater than a threshold value (conditions C). The threshold value of the amount of motion included in the conditions A and the threshold of the amount of motion included in the conditions B may be the same values, or may be different values.

Figure 8A:
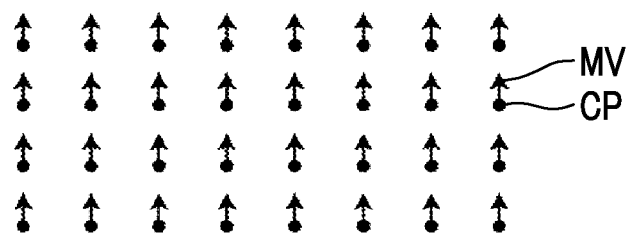
FIG. 8A is a diagram showing control points and motion vectors of the control points.
Figure 8B:
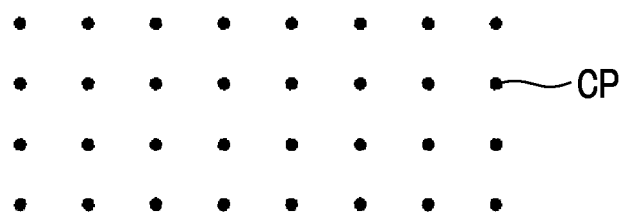
FIG. 8B is a diagram showing control points and motion vectors of the control points.
Figure 8C:
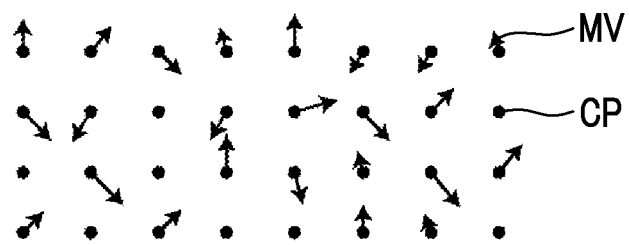
FIG. 8C is a diagram showing control points and motion vectors of the control points.

FIGS. 8A to 8C show control points and motion vectors of the control points. In FIGS. 8A to 8C, a motion vector MV of each control point CP is shown by an arrow extending from each control point. Here, in a position range including eight control points in the horizontal direction of the image and four control points in the vertical direction of the image, it is determined whether or not the motion detected at each of a plurality of control points satisfies predetermined conditions. This position range corresponds to the position range that is raster-scanned in FIG. 7. The region of interest setting means 32 determines whether or not the motion vector MV of each control point CP satisfies the predetermined conditions in such a position range.

In a case where each control point translates in the same direction by the same amount between frames, as shown in FIG. 8A, the motion vectors MV of the respective control point CP are oriented in the same direction, and the magnitudes of the motion vectors MV of the respective control point CP are almost the same. It is thought that a hard substance such as a bone, which is displaced as the contact pressure of the probe 11 changes, is present in the region of the photoacoustic image in which there is a control point that translates between frames as described above. Since it is thought that there is no blood flow in a portion where a hard substance is present, it is preferable to exclude the position range, in which the control point CP that translates is present, from the region of interest for generating blood flow information.

The region of interest setting means 32 determines whether or not the motion detected at each of a plurality of control points included in the position range satisfies the conditions A. That is, it is determined whether or not the amount of motion detected at each of a plurality of control points is equal to or greater than the threshold value and the difference in the direction of the motion detected at each of a plurality of control points and the difference in the amount of motion detected at each of a plurality of control points are within a threshold value (allowable range). In a case where the motion detected at each of a plurality of control points included in the above position range satisfies the conditions A, the position range is determined to be a position range that translates, and a region of interest candidate including the position range is excluded from the regions of interest.

On the other hand, in a case where each control point does not move between frames, as shown in FIG. 8B, the motion vector MV is set to approximately 0 (zero vector) at each control point CP. It is thought that the region of the photoacoustic image, in which there is a control point that does not move between frames as described above, is a region where the contact pressure by the probe 11 is not applied. In such a region, the blood flow does not change before and after avascularization. Therefore, it is preferable to exclude the position range where there is the control point CP, which does not move between frames, from the region of interest for generating blood flow information.

The region of interest setting means 32 determines whether or not the motion detected at each of a plurality of control points included in the position range satisfies the conditions B. That is, it is determined whether or not the amount of motion detected at each of a plurality of control points is smaller than the threshold value. In a case where the motion detected at each of a plurality of control points included in the above position range satisfies the conditions B, the position range is determined to be a position range where the contact pressure by the probe 11 is not applied, and a region of interest candidate including the position range is excluded from the regions of interest.

In a case where the signal strength of the detection signal of the photoacoustic wave detected at each control point is weak, as shown in FIG. 8C, the variation of the motion vector MV between the control points CP is large, and the direction of the motion detected at each control point and the amount of motion detected at each control point are random. The reason why the variation of the motion vector between the control points CP is large as described above is thought to be due to a large noise component and a failure in matching in calculating the motion vector. Since it is thought that a photoacoustic wave cannot be detected significantly by the probe 11 in the position range where the variation of the motion vector MV between the control points CP is large, it is preferable to exclude the position range where the variation of the motion vector MV between the control points CP is large from the region of interest for generating blood flow information.

The region of interest setting means 32 determines whether or not the motion detected at each of a plurality of control points included in the position range satisfies the conditions C. That is, it is determined whether or not at least one of the variation in the direction of the motion detected at each of a plurality of control points or the variation in the amount of motion detected at each of a plurality of control points is equal to or greater than the threshold value. The region of interest setting means 32 determines whether or not the conditions C are satisfied, for example, by scoring the degree of variation based on the variance value of motion (motion vector) detected at a plurality of control points included in the position range or the relationship between the motion vectors of control points adjacent to each other in the coordinate axis and/or time axis direction. In a case where the motion detected at each of a plurality of control points included in the above position range satisfies the conditions C, the position range is determined to be a position range where the photoacoustic wave cannot be detected dominantly by the probe 11, and a region of interest candidate including the position range is excluded from the regions of interest.

Figure 9A:
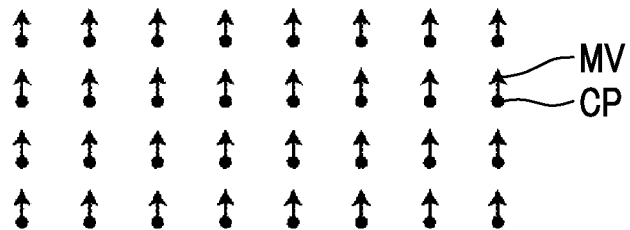
FIG. 9A is a diagram showing a predetermined position range.
Figure 9B:
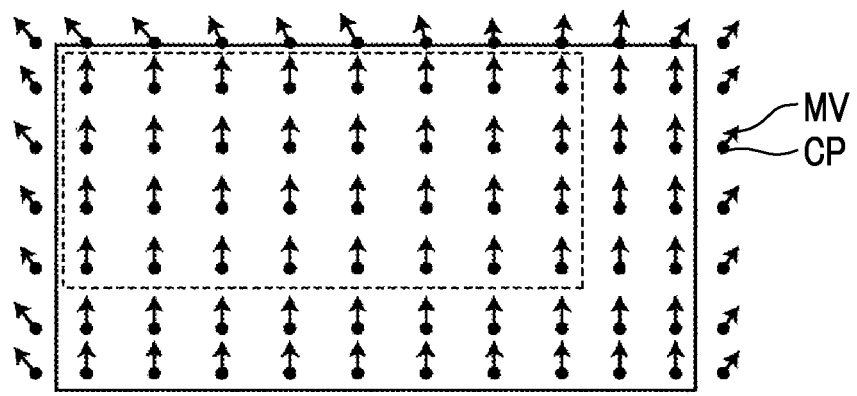
FIG. 9B is a diagram showing an enlarged position range.

In a case where the motion detected at each of a plurality of control points included in the position range satisfies predetermined conditions, the region of interest setting means 32 may determine whether or not the motion detected at each of a plurality of control points including control points adjacent to the position range satisfies the predetermined conditions, and enlarge the position range until the conditions are not satisfied. FIG. 9A shows a predetermined position range, and FIG. 9B shows an enlarged position range. For example, as shown in FIG. 9A, it is assumed that the conditions A (translation) are satisfied in a position range of 8 (horizontal)×4 (vertical) control points. The region of interest setting means 32 determines whether or not the conditions A are satisfied including control points outside the 8 (horizontal)×4 (vertical) control points, and enlarges the position range until the conditions A are not satisfied.

In a case where it is determined that the conditions A are satisfied in a certain position range, the region of interest setting means 32 determines whether or not the conditions A are satisfied including control points adjacent to the position range in the vertical direction and/or the horizontal direction. Specifically, the magnitude and direction of the motion vector of each control point included in the position range where it is determined that the conditions A are satisfied are compared with the magnitude and direction of the motion vector of an adjacent control point, and it is determined whether or not the difference is within an allowable range. In a case where the difference is within the allowable range, it is further determined whether or not the conditions A are satisfied including an adjacent control point. By repeating the work until the conditions A are not satisfied, it is possible to search for a range translating beyond the original position range, for example, as shown in FIG. 9B.

In a case where the position range satisfying the predetermined conditions matches a region of interest candidate, the region of interest setting means 32 may exclude the region of interest candidate from regions of interest. In a case where the position range satisfying the predetermined conditions does not overlap the entire region of interest candidate but overlaps a part of the region of interest candidate, the region of interest candidate may be excluded from the regions of interest. Alternatively, the area of the region of interest candidate may be compared with the area of a portion where the region of interest candidate overlaps the position range satisfying the predetermined conditions, and the region of interest candidate may be excluded from the regions of interest in a case where the percentage of the area of the overlapping portion is equal to or greater than a predetermined value.

Similarly in the time axis direction, in a case where the motion detected at each of a plurality of control points included in the position range satisfies predetermined conditions in a predetermined time range, the region of interest setting means 32 may determine whether or not the motion detected at each of a plurality of control points including the time before and after the time range satisfies the predetermined conditions and enlarge the time range until the conditions are not satisfied. In the case of enlarging the position range or the time range, in order to prevent a determination error due to mismatching of a specific control point, it is preferable to add processing for excluding outliers by robust estimation or the like.

Figure 10:
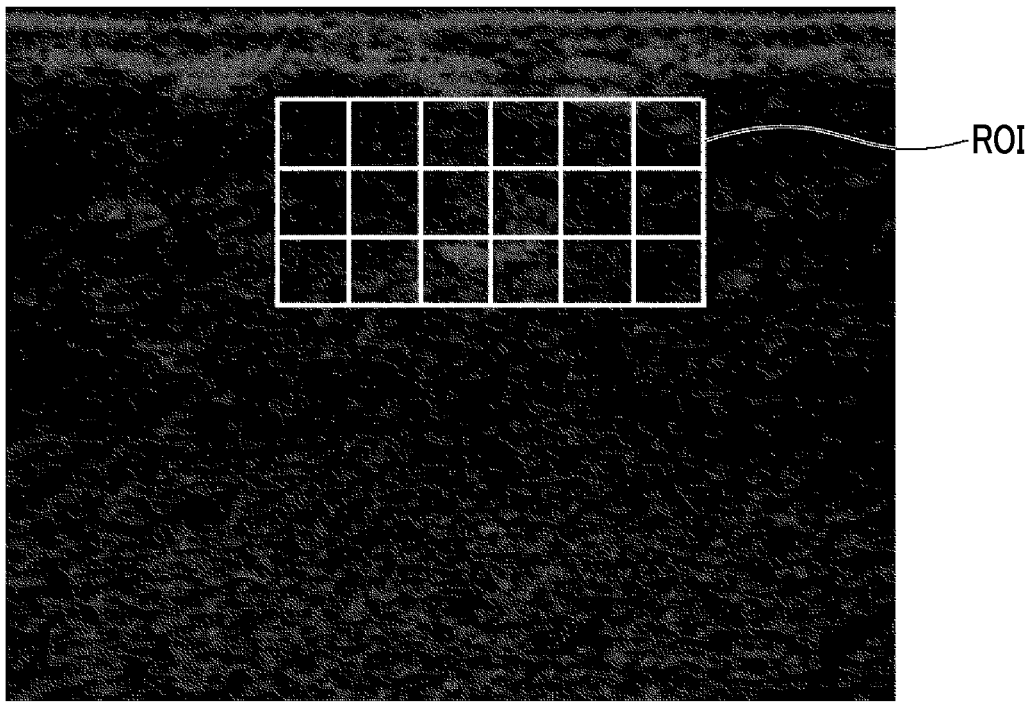
FIG. 10 is a diagram showing a region of interest set by region of interest setting means.

FIG. 10 shows a region of interest set by the region of interest setting means 32. For example, in the initial state, the region of interest setting means 32 sets all the region of interest candidates shown in FIG. 5 as regions of interest. The region of interest setting means 32 determines region of interest candidates, which are to be excluded from the regions of interest, based on the motion of the control point in the photoacoustic image detected by the motion detection means 31. The region of interest setting means 32 sets a region of interest candidate, which is not excluded from the region of interest candidates, as a region of interest ROI. In FIG. 10, as a result of excluding region of interest candidates including the position range satisfying the predetermined conditions from the regions of interest by the region of interest setting means 32, each of 6 (horizontal)×3 (vertical) region of interest candidates is set as the region of interest ROI.

Figure 11:
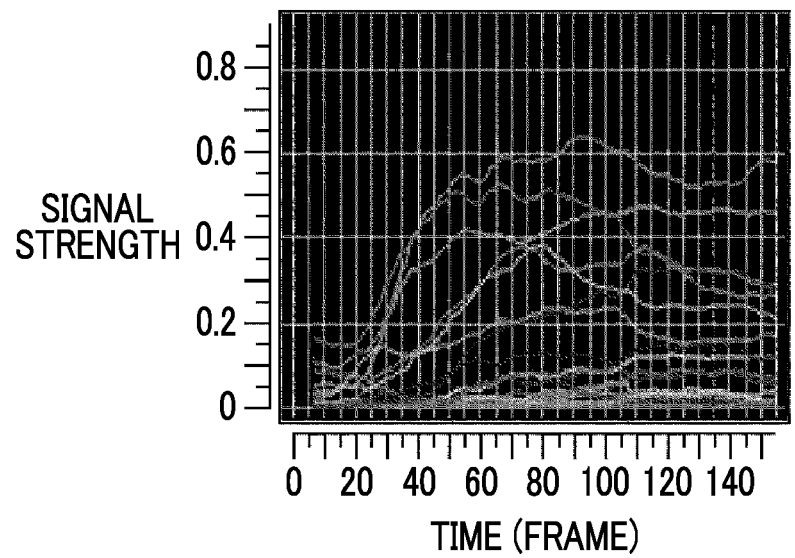
FIG. 11 is a graph showing a temporal change in blood flow information.

FIG. 11 is a graph showing a temporal change in blood flow information. For each region of interest ROI shown in FIG. 10, the blood flow information generation means 27 calculates an average value (ROI signal value) of the signal strengths of the regions of interest ROI, and generates a graph showing a temporal change in the ROI signal value. In the case of displaying the region of interest ROI and the graph, the display color of the region of interest ROI and the display color of the graph may be set to the same color so that it is possible to distinguish which graph corresponds to which region of interest ROI. By observing the temporal change in the ROI signal value, it is possible to evaluate the blood flow information.

Figure 12:
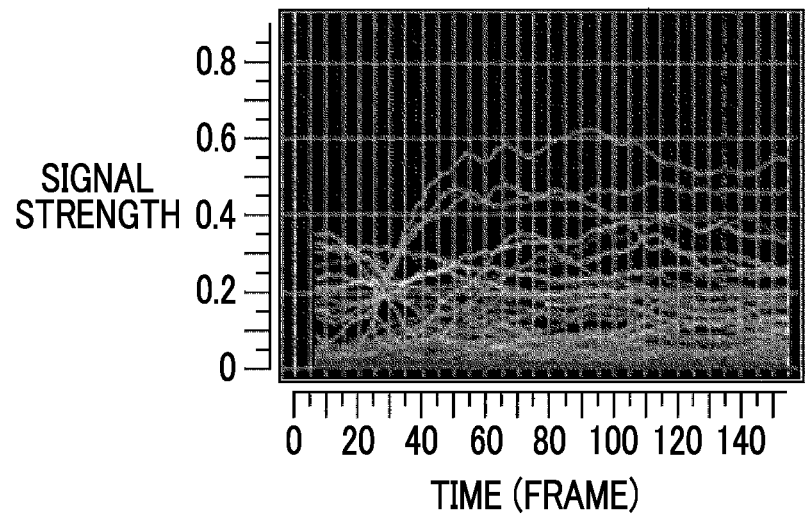
FIG. 12 is a graph showing a temporal change in blood flow information in a case where all region of interest candidates are set as regions of interest.

As a comparative example, FIG. 12 shows a graph showing a temporal change in blood flow information in a case where all the region of interest candidates shown in FIG. 5 are set as regions of interest. In the comparative example, regions of interest are set in a number of photoacoustic images. Accordingly, in a case where a graph showing a temporal change in blood flow information is generated and displayed for each of the regions of interest, a lot of information is displayed at a time. The display is hard to see. In contrast, in the present embodiment, since a graph showing a temporal change in blood flow information is generated and displayed for a limited number of regions of interest, it is easy to evaluate the blood flow information.

Figure 13:
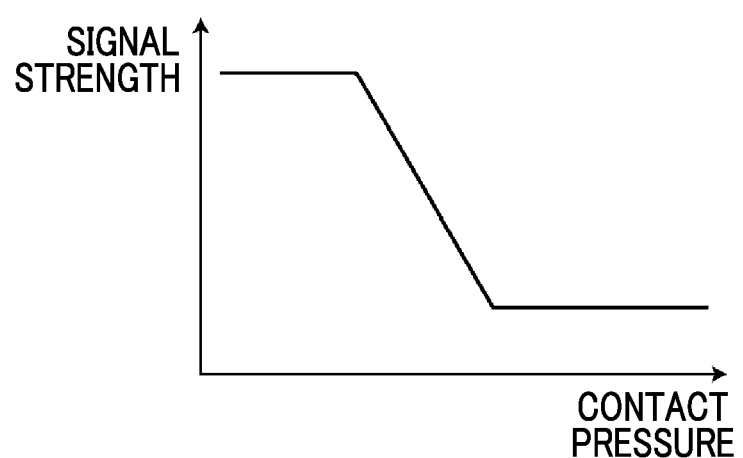
FIG. 13 is a graph showing the relationship between blood flow information and the contact pressure of a probe.

The blood flow information generation means 27 may further generate a graph showing the relationship between blood flow information and the contact pressure (avascularization pressure) of the probe 11. FIG. 13 is a graph showing the relationship between blood flow information (ROI signal value) and the contact pressure of the probe 11. In a case where the ROI signal value is plotted with respect to the contact pressure of the probe 11, the graph shown in FIG. 13 is obtained. This graph is generated for each region of interest. By referring to this graph, it is possible to know the contact pressure at which perfusion of blood starts, the inclination of the ROI signal value with respect to the contact pressure, the contact pressure at which the blood flow reaches a level before the avascularized condition, and the like. Therefore, it is possible to evaluate the perfusion of the subject.

Although an example in which the average value or the total value (ROI signal value) of the signal strength of the photoacoustic image in the region of interest is used as blood flow information has been described above, the blood flow information is not limited thereto. Instead of using the ROI signal value itself as the blood flow information, a score value obtained by converting the ROI signal value using a look-up table, a function, or the like may be used as the blood flow information.

The blood flow information generation means 27 may generate, as the blood flow information, a score value based on the difference between the maximum value and the minimum value of the ROI signal value within a certain period. Alternatively, the blood flow information generation means 27 may generate, as the blood flow information, a score value based on the difference between the ROI signal value in the avascularized condition and the ROI signal value in the non-avascularized condition. Alternatively, the blood flow information generation means 27 may generate, as the blood flow information, a score value based on a time change rate of the ROI signal value in a case where the avascularized condition is changed to the non-avascularized condition. The time change rate can be calculated, for example, by differentiating the ROI signal value with time.

The blood flow information generation means 27 may generate, as the blood flow information, a score value based on the time from the reference time to the time, at which the ROI signal value reaches a certain level, in a case where the avascularized condition is changed to the non-avascularized condition. Alternatively, the blood flow information generation means 27 may generate, as the blood flow information, a score value based on the ROI signal value at a time when a certain time has passed from the reference time in a case where the avascularized condition is changed to the non-avascularized condition. The reference time may be, for example, a time at which the avascularized condition is changed to the non-avascularized condition. Alternatively, a time at which the contact pressure of the probe 11 starts to change stepwise may be set as the reference time. By using the blood flow information, it is possible to evaluate the extent or the speed of blood increase due to perfusion.

The blood flow information generation means 27 may further generate a blood flow information image based on the blood flow information. The blood flow information image generated by the blood flow information generation means 27 is a space map image for displaying the blood flow information of each region of interest in the region of interest. In the blood flow information image, each region of interest is displayed with a brightness corresponding to the blood flow information. By map-displaying the blood flow information, it becomes easy to compare the pieces of blood flow information between a plurality of regions of interest.

The blood flow information generation means 27 generates a blood flow information image in time series, for example. In this case, the blood flow information generation means 27 may set the display color of each region of interest in the blood flow information image to a different display color in a case where blood flow information at the first time is larger than blood flow information at the second time earlier than the first time and a case where the blood flow information at the first time is smaller than the blood flow information at the second time. One example of the first time is, for example, a current time. As a more specific example, the first time is a (current) time at which the blood flow information image is displayed on the screen. However, the first time is not limited thereto. For example, red may be set as a display color for a part where the blood flow is increasing and the blood flow information at the first time is larger than the blood flow information at the second time, and blue may be set as a display color for a part where the blood flow is decreasing and the blood flow information at the first time is smaller than the blood flow information at the second time. In this case, by referring to the blood flow information image, it becomes easy to understand in which part the blood has increased and in which part the blood has decreased.

Here, since the ROI signal value depends on the signal strength of the detection signal of the photoacoustic wave, the ROI signal value is strongly influenced by a relatively thick blood vessel having a large blood flow (having a large signal strength) or the like. In order to evaluate the blood perfusion state of a fine blood vessel for nourishing the tissue, it is preferable to perform evaluation using an amount that does not depend on the signal strength, for example, a binary amount. It is preferable that binarization is performed so as to distinguish between a range from a lower threshold value to an upper threshold value and the outside of the range. For example, the blood flow information generation means 27 may binarize the signal strength of the photoacoustic image by setting the signal strength of the photoacoustic image to a first value (for example, a signal value 1) in a case where the signal strength of the photoacoustic image is equal to or greater than a first threshold value (corresponding to a lower threshold value) and equal to or less than a second threshold value (corresponding to an upper threshold value) larger than the first threshold value and setting the signal strength of the photoacoustic image to a second value (for example, a signal value 0) in a case where the signal strength of the photoacoustic image is less than the first threshold value or greater than the second threshold value, and generate the blood flow information based on the binarized signal strength of the photoacoustic image. More specifically, the blood flow information generation means 27 may add binarized values in a region of interest and generate blood flow information based on a value standardized by the area of the region of interest.

In the present embodiment, a photoacoustic image is generated by performing light emission and photoacoustic wave detection while changing the avascularization pressure between the avascularized condition and the non-avascularized condition, and the motion of the control point in the photoacoustic image is detected. A region of interest is set based on the motion detected at the control point, and blood flow information is generated based on the signal strength of the photoacoustic image in the region of interest. By setting the region of interest based on the motion of the control point, a region of interest useful for the evaluation of blood flow can be set even in a case where a photoacoustic image with little structure information of the subject and with few features as markers is used.

In the present embodiment, a region of interest is set among a plurality of region of interest candidates set in a lattice form. In the setting of a region of interest, a region of interest candidate to be excluded from the regions of interest among a plurality of region of interest candidates is determined based on the motion detected at the control point included in each region of interest candidate. In particular, it is determined whether or not the motion detected at each of a plurality of control points, which are included in the position range including a plurality of control points, satisfies predetermined conditions, and a region of interest candidate to be excluded from the regions of interest is determined based on the determination result. For example, in a case where the motion detected at a control point included in a certain position range indicates translation, no motion, and/or random motion, a region of interest candidate including the position range is excluded from the regions of interest. In this manner, an unnecessary region of interest candidate can be excluded from the regions of interest. As a result, it can be avoided that evaluation becomes difficult due to too many regions of interest.

Although an example in which light having a wavelength of 755 nm is mainly used as the measurement light has been described above, the wavelength of the measurement light is not limited thereto. For example, light having a wavelength of 1064 nm or 800 nm may be used as the measurement light.

The number of wavelengths of the measurement light is not limited to one, and measurement light having a plurality of wavelengths may be used. As described above, the strength of the photoacoustic wave generated in the subject changes depending on the hemoglobin concentration and the oxygen saturation, and the manner of the change varies depending on the wavelength of the measurement light. For example, in a case where the wavelength of the measurement light is 755 nm, a stronger photoacoustic wave is generated from a vein having lower oxygen saturation between the artery and the vein. In a case where the wavelength of the measurement light is 1064 nm, a stronger photoacoustic wave is generated from the artery having higher oxygen saturation. In other words, in a case where the wavelength of the measurement light is 755 nm, the detection signal of the photoacoustic wave increases in a case where the oxygen saturation is low. In a case where the wavelength of the measurement light is 1064 nm, the detection signal of the photoacoustic wave increases in a case where the oxygen saturation is high. In a case where the wavelength of the measurement light is 800 nm, the generated photoacoustic wave hardly changes with the oxygen saturation. By detecting a photoacoustic wave using light having a wavelength of 755 nm and light having a wavelength of 1064 nm as the measurement light and examining the wavelength dependence of the detection signal of the photoacoustic wave, the blood flow and the oxygen saturation can be separated. The combination of wavelengths is not limited to those described above. For example, light having a wavelength of 755 nm and light having a wavelength of 800 nm may be used as the measurement light. Thus, since the blood flow and the oxygen saturation can be separated by using the measurement light having a plurality of wavelengths, the blood flow information generation means 27 can generate blood flow information relevant to the oxygen saturation instead of or in addition to the blood flow information relevant to the blood flow.

Figure 14:
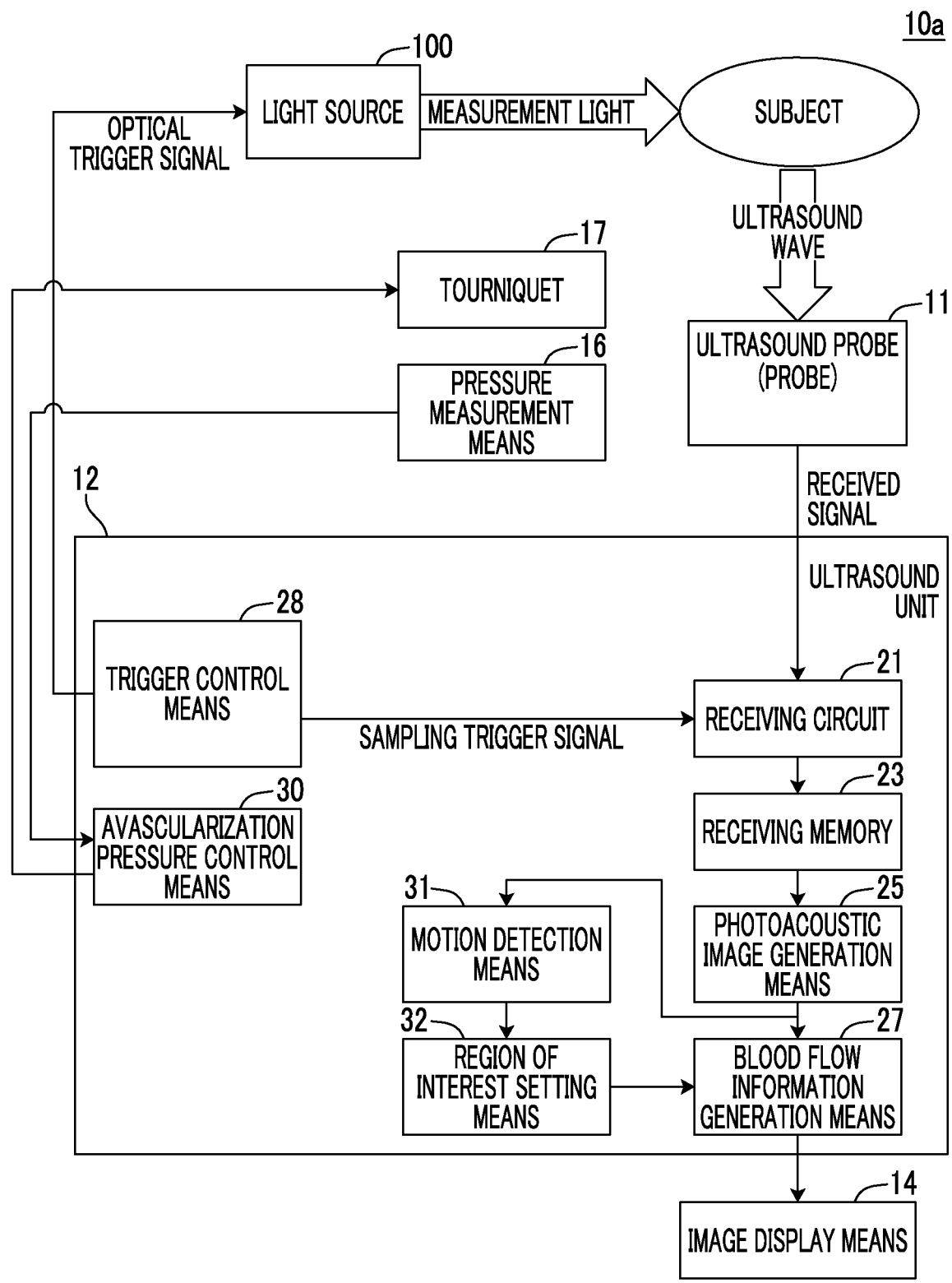
FIG. 14 is a block diagram showing a photoacoustic measurement system according to a second embodiment of the present invention.

Subsequently, a second embodiment of the present invention will be described. FIG. 14 shows a photoacoustic measurement system according to the second embodiment of the present invention. A photoacoustic measurement system 10a of the present embodiment has pressure measurement means 16 and a tourniquet 17 in addition to the configuration of the photoacoustic measurement system according to the first embodiment shown in FIG. 2. In the present embodiment, avascularization is performed separately using the tourniquet 17. Others may be the same as in the first embodiment. In the present embodiment, the stage 15 (refer to FIGS. 1 and 2) may be omitted.

The tourniquet 17 is a tourniquet with variable cuff pressure. At the time of measurement, the tourniquet 17 is disposed at a position closer to the heart than the measurement part of the subject, for example, on the upper arm of the subject. It is possible to increase the cuff pressure by supplying air to the tourniquet 17 using a pump or the like attached to the tourniquet 17 and to reduce the cuff pressure by opening the exhaust valve. The pressure measurement means 16 is, for example, a pressure sensor, and detects the cuff pressure of the tourniquet 17.

The avascularization pressure control means 30 controls the cuff pressure of the tourniquet 17. The avascularization pressure control means 30 controls the cuff pressure of the tourniquet 17 to be a desired pressure based on the cuff pressure detected by the pressure measurement means 16. In a case where the measurement is started, the avascularization pressure control means 30 increases the cuff pressure of the tourniquet 17 so that the subject becomes in the avascularized condition. Then, after maintaining the avascularized condition for a certain period of time, the cuff pressure is reduced stepwise so that the subject becomes in the non-avascularized condition. In the meantime, emission of measurement light to the subject and detection of photoacoustic waves are continued. Instead of gradually reducing the cuff pressure, the cuff pressure may be abruptly reduced to the non-avascularized condition.

In the present embodiment, the tourniquet 17 (another example of avascularization means) is used for avascularization of the subject. It is possible to obtain the same effect as the effect obtained by the photoacoustic measurement apparatus according to the first embodiment including the effect that a region of interest useful for the evaluation of blood flow can be set. In the present embodiment, instead of controlling the avascularization pressure by the avascularization pressure control means 30, the avascularization pressure may be controlled manually.

Figure 15:
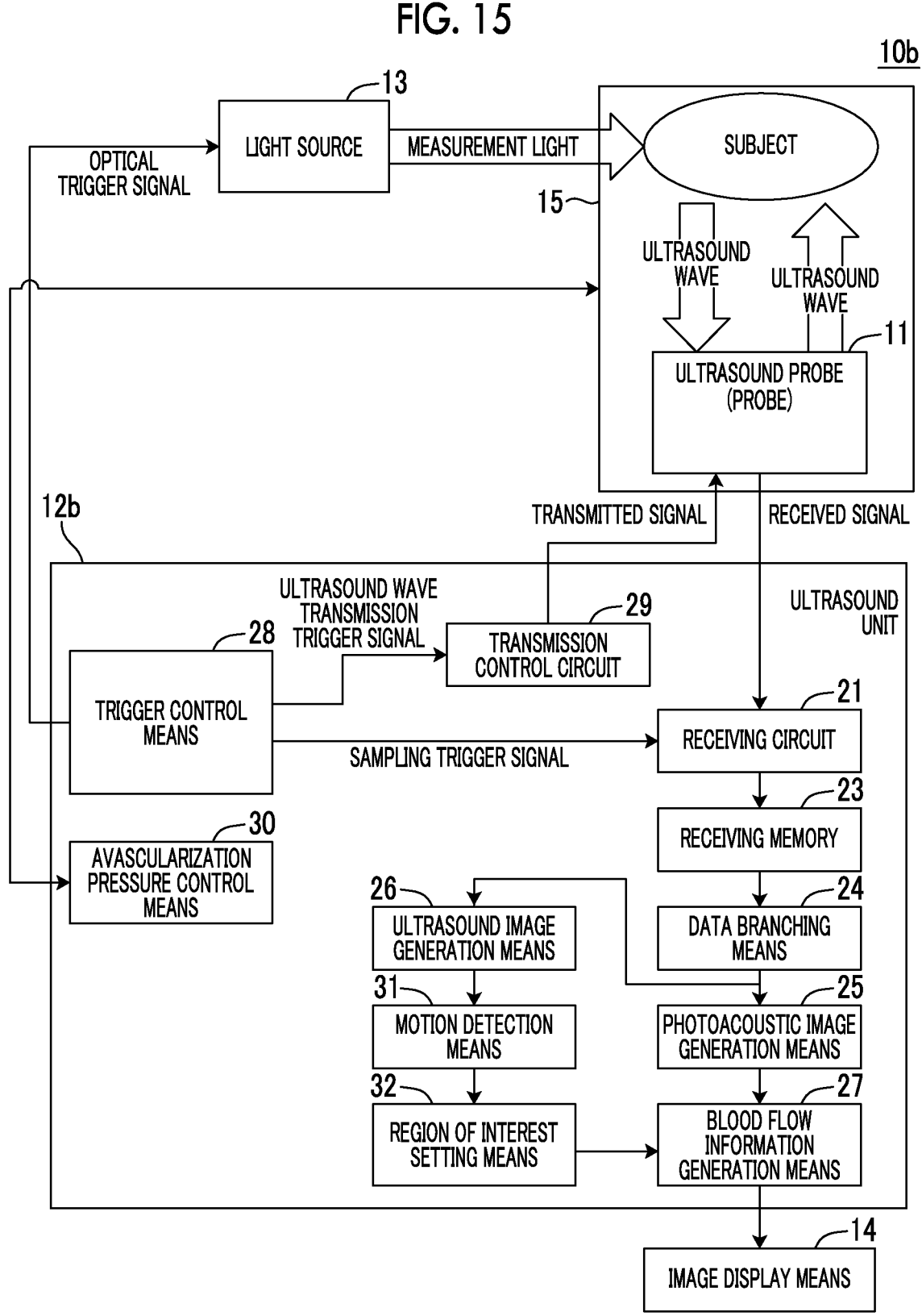
FIG. 15 is a block diagram showing a photoacoustic measurement system according to a third embodiment of the present invention.

Subsequently, a third embodiment of the present invention will be described. FIG. 15 shows a photoacoustic measurement system according to the third embodiment of the present invention. A photoacoustic measurement system 10b of the present embodiment is different from the photoacoustic measurement system 10 of the first embodiment shown in FIG. 2 in that an ultrasound unit 12b further has data branching means 24, ultrasound image generation means 26, and a transmission control circuit 29. Others are the same as those in the first embodiment or the second embodiment. In the embodiment of the present invention, an ultrasound wave is used as an acoustic wave. However, the acoustic wave is not limited to the ultrasound wave, and an acoustic wave having an audible frequency may be used as long as an appropriate frequency can be selected according to an examination target, measurement conditions, or the like.

In the present embodiment, in addition to the detection of photoacoustic waves, the probe 11 performs transmission of acoustic waves (ultrasound waves) to the subject and reception of reflected acoustic waves (reflected ultrasound waves) of the transmitted ultrasound waves. In addition, transmission and reception of sound waves may be performed at separate positions. For example, ultrasound waves may be transmitted from a position different from the probe 11, and reflected ultrasound waves of the transmitted ultrasound waves may be received by the probe 11.

The probe 11 outputs a detection signal of photoacoustic waves and a detection signal of reflected ultrasound waves, and detection signals (sampling data) of photoacoustic waves and reflected ultrasound waves after AD conversion are stored in the receiving memory 23. The data branching means 24 is, for example, a changeover switch, and transmits the sampling data of the detection signal of photoacoustic waves read from the receiving memory 23 to the photoacoustic image generation means 25. In addition, the sampling data of the reflected ultrasound waves read from the receiving memory 23 is transmitted to the ultrasound image generation means 26.

The ultrasound image generation means (reflected acoustic wave image generation means) 26 generates an ultrasound image (reflected acoustic wave image) based on the detection signal of reflected ultrasound waves detected by the probe 11. The generation of an ultrasound image also includes image reconstruction such as phase matching addition, detection, and logarithmic conversion. The generated ultrasound image may be displayed on the image display means 14. The ultrasound image generation means 26 is, for example, a DSP. The function of the ultrasound image generation means 26 may be realized by software processing using a processor included in the ultrasound unit 12b.

In the case of acquiring an ultrasound image, the trigger control means 28 transmits an ultrasound wave transmission trigger signal for giving an instruction to transmit ultrasound waves to the transmission control circuit 29. In a case where the ultrasound wave transmission trigger signal is received, the transmission control circuit 29 makes the probe 11 transmit ultrasound waves. The probe 11 detects reflected ultrasound waves by performing a scan while shifting the acoustic line by one line at a time, for example. The trigger control means 28 transmits a sampling trigger signal to the receiving circuit 21 according to the timing of ultrasound wave transmission, thereby starting the sampling of reflected ultrasound waves. Acquisition of a photoacoustic image and acquisition of an ultrasound image may be performed in synchronization with each other.

Based on the ultrasound images at a plurality of times generated by the ultrasound image generation means 26, the motion detection means 31 detects the motion of the ultrasound image at each of a plurality of positions corresponding to the plurality of control points set in the photoacoustic image. For convenience, the plurality of positions of the ultrasound images corresponding to the plurality of control points set in the photoacoustic image are also referred to as control points. The motion detection means 31 regards the motion of each control point in the detected ultrasound image as the motion of each control point set in the photoacoustic image. The setting of the region of interest in the region of interest setting means 32 is the same as that in the first embodiment. It is preferable that the photoacoustic image and the ultrasound image are aligned using a known method.

Figure 16:
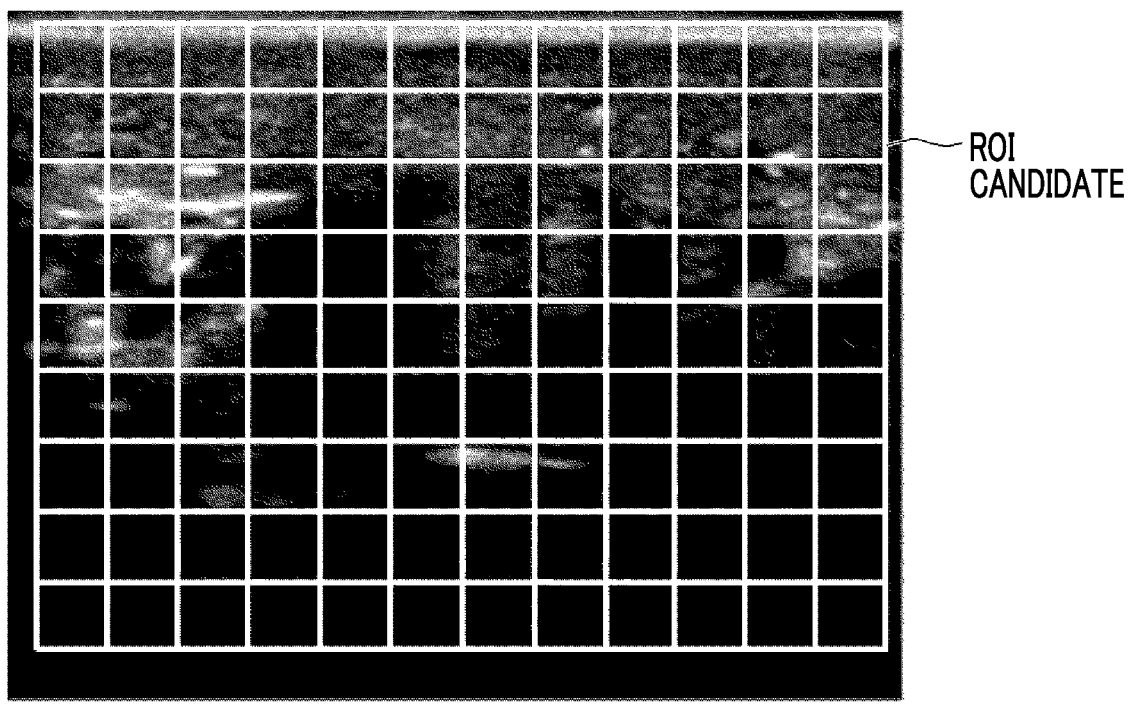
FIG. 16 is a diagram showing an ultrasound image and region of interest candidates.

FIG. 16 shows an ultrasound image and region of interest candidates. The position of each region of interest candidate (ROI candidate) set in the ultrasound image shown in FIG. 16 corresponds to the position of each region of interest candidate (ROI candidate) set in the photoacoustic image shown in FIG. 5. In the ultrasound image, control points are set at positions corresponding to the control points set in the photoacoustic image, and the region of interest candidate in the ultrasound image also includes a plurality of control points. The motion detection performed by the motion detection means 31 is the same as that in the first embodiment except that an image used for detection is changed from the photoacoustic image to the ultrasound image.

Figure 17:
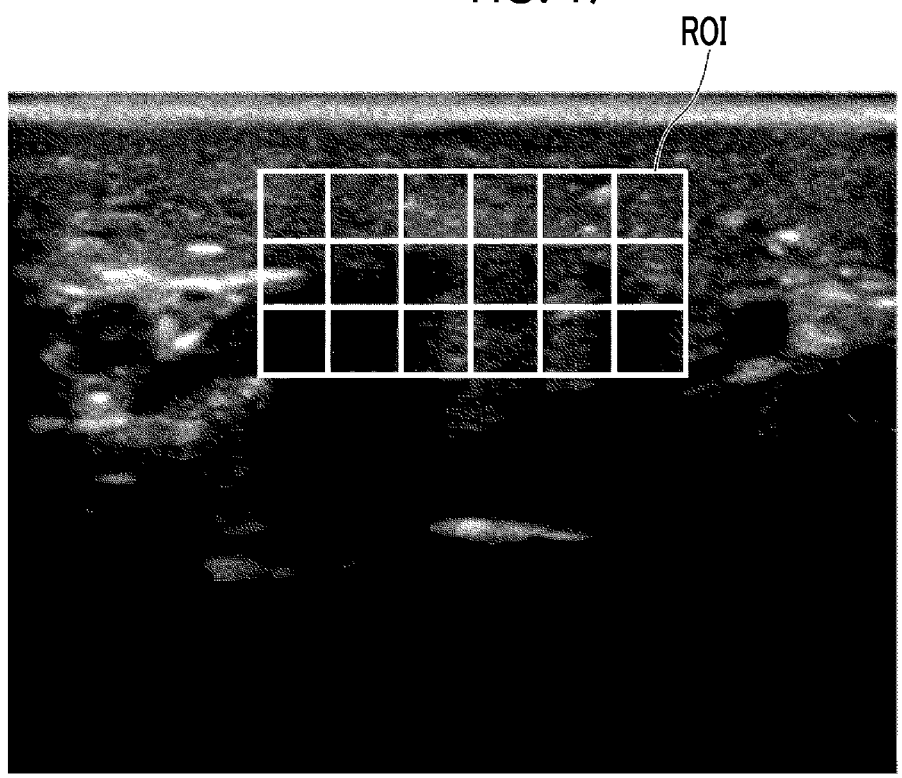
FIG. 17 is a diagram showing an ultrasound image and regions of interest.

FIG. 17 shows an ultrasound image and regions of interest. For example, the region of interest setting means 32 sets all region of interest candidates as regions of interest in the initial state, and excludes a region of interest candidate included in a position range, in which the motion detected at each of the plurality of control points satisfies predetermined conditions, from regions of interest. In FIG. 17, 6 (horizontal)×3 (vertical) region of interest candidates are set as the regions of interest ROI. The blood flow information generation means 27 generates the blood flow information of the regions of interest ROI set in this manner.

In the present embodiment, an ultrasound image acquired in synchronization with a photoacoustic image is used for motion detection. Performing the motion detection in the ultrasound image is equivalent to setting the region of interest in the ultrasound image. In a case where the photoacoustic image and the ultrasound image are compared with each other, the ultrasound image has a higher signal to noise ratio (SNR) than the photoacoustic image. In addition, the ultrasound image has more structure information of the subject. For this reason, in a case where the ultrasound image is used, it is possible to detect motion with high accuracy compared with a case in which the photoacoustic image is used. Therefore, in the present embodiment, it is possible to set the region of interest more appropriately compared with the first embodiment or the second embodiment. Other effects are the same as those of the first embodiment or the second embodiment.

While the present invention has been described based on the preferred embodiments, the photoacoustic measurement apparatus and system of the present invention are not limited to the above embodiments, and various modifications and changes in the configurations of the above embodiments are also included in the range of the present invention.

EXPLANATION OF REFERENCES

10: photoacoustic measurement system
11: probe
12: ultrasound unit
13: light source
14: image display means
15: stage
16: pressure measurement means
17: tourniquet
21: receiving circuit
23: receiving memory
24: data branching means
25: photoacoustic image generation means
26: ultrasound image generation means
27: blood flow information generation means
28: trigger control means
29: transmission control circuit
30: avascularization pressure control means
31: motion detection means
32: region of interest setting means
51: grip portion
52: moving mechanism
53: pressure measurement means

What is claimed is:
1. A photoacoustic measurement apparatus, comprising:
a receiving circuit that receives detection signals obtained by detecting photoacoustic waves generated in a subject by emission of measurement light to the subject;
photoacoustic image generating circuitry for generating a plurality of photoacoustic images, each of the plurality of photoacoustic images being generated based on the detection signals of the photoacoustic waves;
processing circuitry configured to:
detect motion of each of a plurality of control points set in the plurality of the photoacoustic images, which are generated by emitting the measurement light to the subject at a plurality of times between an avascularized condition and a non-avascularized condition, using the plurality of the photoacoustic images;
set a region of interest based on the motion detected at each control point included in a position range including the plurality of control points; and
generate blood flow information based on a signal strength of one of the plurality of the photoacoustic images in the region of interest.

2. A photoacoustic measurement apparatus, comprising:
a receiving circuit that receives detection signals of photoacoustic waves generated in a subject by emission of measurement light to the subject and detection signals of reflected acoustic waves of acoustic waves transmitted to the subject;
photoacoustic image generating circuitry for generating a plurality of photoacoustic images based on the detection signals of the photoacoustic waves;
processing circuitry configured to:
generate a plurality of reflected acoustic wave imago images based on the detection signals of the reflected acoustic waves;
detect motion of each of the plurality of the reflected acoustic wave images, which are generated by transmitting the acoustic waves to the subject at a plurality of times between an avascularized condition and a non-avascularized condition, at a plurality of positions corresponding to a plurality of control points set in one of the plurality of photoacoustic images using the plurality of the reflected acoustic wave images and detect the detected motion at each position as motion of each control point set in the one of the plurality of photoacoustic images;
set a region of interest based on the motion detected at each control point included in a position range including the plurality of control points; and
generate blood flow information based on a signal strength of the one of the plurality of photoacoustic images in the region of interest.

3. The photoacoustic measurement apparatus according to claim 1,
wherein a plurality of region of interest candidates are set in a lattice form in the one of the plurality of photoacoustic images, and each region of interest candidate includes the plurality of control points, and
the processing circuitry determines a region, which is to be set as the region of interest, among the plurality of region of interest candidates.

4. The photoacoustic measurement apparatus according to claim 3,
wherein the processing circuitry sets the region of interest by determining a region of interest candidate to be excluded from the plurality of the region of interest candidates and setting remaining regions of interest candidates as regions of interest.

5. The photoacoustic measurement apparatus according to claim 4,
wherein, based on the motion detected at each control point included in each region of interest candidate, the processing circuitry determines whether or not to exclude the region of interest candidate from the region of interest.

6. The photoacoustic measurement apparatus according to claim 4,
wherein the processing circuitry determines whether or not the motion detected at each of the plurality of control points included in the position range satisfies predetermined conditions, and determines the region of interest candidate to be excluded based on the determination result.

7. The photoacoustic measurement apparatus according to claim 6,
wherein, in a case where the motion detected at each of the plurality of control points included in the position range satisfies the conditions, the processing circuitry determines whether or not the motion detected at each of a plurality of control points including control points adjacent to the position range satisfies the conditions, and enlarges the position range until the conditions are not satisfied.

8. The photoacoustic measurement apparatus according to claim 6,
wherein the processing circuitry determines whether or not the motion detected at each of the plurality of control points included in the position range satisfies the conditions in a predetermined time range, and determines the region of interest candidate to be excluded based on the determination result.

9. The photoacoustic measurement apparatus according to claim 8,
wherein, in a case where the motion detected at each of the plurality of control points included in the position range satisfies the conditions in the time range, the processing circuitry determines whether or not motion detected at each of the plurality of control points including a time before and after the time range satisfies the conditions, and enlarges the time range until the conditions are not satisfied.

10. The photoacoustic measurement apparatus according to claim 6,
wherein the processing circuitry determines a region of interest candidate, which includes a position range where the motion detected at each of the plurality of control points satisfies the conditions, as the region of interest candidate to be excluded.

11. The photoacoustic measurement apparatus according to claim 10,
wherein the conditions include at least one of conditions in which an amount of motion detected at each of the plurality of control points is equal to or greater than a threshold value and each of a difference in a direction of the motion detected at each of the plurality of control points and a difference in the amount of motion detected at each of the plurality of control points is within a threshold value, conditions in which the amount of motion detected at each of the plurality of control points is less than a threshold value, or conditions in which at least one of a degree indicating a variation in the direction of the motion detected at each of the plurality of control points or a degree indicating a variation in the amount of motion detected at each of the plurality of control points is equal to or greater than a threshold value.

12. The photoacoustic measurement apparatus according to claim 3,
wherein the processing circuitry determines whether or not the motion detected at each of the plurality of control points included in the position range satisfies predetermined conditions, and sets a region of interest candidate, which includes a position range where the motion detected at each of the plurality of control points satisfies the conditions, as the region of interest.

13. The photoacoustic measurement apparatus according to claim 1,
wherein the processing circuitry generates, as blood flow information, a total value or an average value of the signal strength in the region of interest.

14. The photoacoustic measurement apparatus according to claim 1,
wherein the processing circuitry further generates a graph showing a relationship between the blood flow information and time.

15. The photoacoustic measurement apparatus according to claim 1, further comprising:
a pressure sensor for measuring an avascularization pressure of the subject,
wherein the processing circuitry further generates a graph showing a relationship between the blood flow information and the avascularization pressure.

16. The photoacoustic measurement apparatus according to claim 1,
wherein the processing circuitry further generates a blood flow information image based on the blood flow information.

17. A photoacoustic measurement system, comprising:
a light source that emits measurement light;
an avascularization device, the device being a probe or a tourniquet, to avascularize a subject while changing avascularization pressure between an avascularized condition and a non-avascularized condition;
acoustic wave detecting circuitry for detecting photoacoustic waves generated in the subject by emission of the measurement light to the avascularized subject;
photoacoustic image generating circuitry for generating a plurality of photoacoustic images based on detection signals of the photoacoustic waves detected by the acoustic wave detecting circuitry;
processing circuitry configured to:
detect a motion of each of a plurality of control points set in the plurality of the photoacoustic images, which are generated by emitting the measurement light at a plurality of times between the avascularized condition and the non-avascularized condition, using the plurality of the photoacoustic images;
set a region of interest based on the motion detected at each control point included in a position range including the plurality of control points; and
generate blood flow information based on a signal strength of one of the plurality of photoacoustic images in the region of interest.

18. A photoacoustic measurement system, comprising:
a light source that emits measurement light;
an avascularization device, the device being a probe or a tourniquet, to avascularize a subject while changing avascularization pressure between an avascularized condition and a non-avascularized condition;
acoustic wave detecting circuitry for detecting photoacoustic waves generated in the subject by emission of the measurement light to the avascularized subject and reflected acoustic waves of an acoustic wave transmitted to the subject;

photoacoustic image generating circuitry for generating a plurality of photoacoustic images based on detection signals of the photoacoustic waves detected by the acoustic wave detecting circuitry;

processing circuitry configured to:
generate a plurality of reflected acoustic wave images based on detection signals of the reflected acoustic waves detected by the acoustic wave detecting circuitry;

detect motion of each of the plurality of the reflected acoustic wave images, which are generated by transmitting the acoustic waves to the subject at a plurality of times between the avascularized condition and the non-avascularized condition, at a plurality of positions corresponding to a plurality of control points set in one of the plurality of photoacoustic images using the plurality of the reflected acoustic wave images and detect the detected motion at each position as a motion of each control point set in the one of the plurality of photoacoustic images;

set a region of interest based on the motion detected at each control point included in a position range including the plurality of control points; and generate blood flow information based on a signal strength of the one of the plurality of photoacoustic images in the region of interest.

* * * * *